(12) United States Patent
Fallon et al.

(10) Patent No.: US 10,214,573 B2
(45) Date of Patent: Feb. 26, 2019

(54) BIGLYCAN VARIANT POLYPEPTIDES AND METHODS OF USE

(71) Applicant: TIVORSAN PHARMACEUTICALS, INC., Saint Louis, MI (US)

(72) Inventors: Justin Fallon, Providence, RI (US); Elizabeth John, Richland, WA (US)

(73) Assignees: Tivorsan Pharmaceuticals, Inc., Saint Louis, MO (US); Brown University, Providence, RI (US)

( * ) Notice: Subject to any disclaimer, the term of this patent is extended or adjusted under 35 U.S.C. 154(b) by 0 days.

(21) Appl. No.: 14/050,225

(22) Filed: Oct. 9, 2013

(65) Prior Publication Data
US 2014/0213523 A1    Jul. 31, 2014

Related U.S. Application Data

(60) Provisional application No. 61/712,177, filed on Oct. 10, 2012.

(51) Int. Cl.
| | | |
|---|---|---|
| A61K 38/00 | (2006.01) | |
| A61K 38/16 | (2006.01) | |
| A61K 39/00 | (2006.01) | |
| C07K 14/47 | (2006.01) | |
| G01N 33/68 | (2006.01) | |
| A61K 38/17 | (2006.01) | |

(52) U.S. Cl.
CPC .......... C07K 14/4725 (2013.01); C07K 14/47 (2013.01); G01N 33/6896 (2013.01); A61K 38/17 (2013.01); G01N 2400/00 (2013.01)

(58) Field of Classification Search
None
See application file for complete search history.

(56) References Cited

U.S. PATENT DOCUMENTS

| | | | |
|---|---|---|---|
| 6,783,961 B1 * | 8/2004 | Edwards et al. | 435/91.1 |
| 6,812,339 B1 * | 11/2004 | Venter et al. | 536/24.31 |
| 7,335,637 B2 | 2/2008 | Fallon et al. | |
| 2010/0197563 A1 * | 8/2010 | Wight | C07K 14/4725 514/1.1 |
| 2012/0004178 A1 * | 1/2012 | Fallon | C07K 14/4725 514/17.7 |

FOREIGN PATENT DOCUMENTS

| | | |
|---|---|---|
| WO | WO 2001/025461 A1 | 4/2001 |
| WO | WO 2003/070195 A2 | 8/2003 |
| WO | WO 2007/088050 A2 | 8/2007 |
| WO | WO 2007/123848 A2 | 11/2007 |
| WO | WO 2008/100789 A2 | 8/2008 |
| WO | WO 2011/146480 A1 | 11/2011 |
| WO | WO 2012/092299 A1 | 7/2012 |

OTHER PUBLICATIONS

Man, Nguyen Thi et al.: "Utrophin, the autosomal homologue of dystrophin, is widely-expressed and membrane-associated in cultured cell lines"; FEBS. 1992, v. 313:1, pp. 19-22.

Matthews, Dennis J. et al.: "Use of Corticosteroids in a Population-Based Cohort of Boys With Duchenne and Becker Muscular Dystrophy"; J. Child Neurol, Nov. 2010, 25: 1319.

Smyth, Gayle M. et al.: "Altered caveolin-3 expression disrupts Pl(3)) kinase signaling leading to death of cultured muscle cells"; Dept. of Neuro and Neurol Sciences, Stanford University, May 23, 2006.

Zhao, Lan et al.: "Targethig Fibrosis in Duchenne Muscular Dystrophy" J Neuropathol Alcurot Aug. 2010 ; 69(8): 771-776.

Adamo, Candace M.: "Sildenafil reverses cardiac dysfunction in the mdx mouse model of Duchenne muscular dystrophy"; PNAS, Nov. 2, 2010; 107(44); 19079-19083.

Amenta, Alison R.: "Biglycan at synapses, the sarcolemma and as a potential therapeutic for Duchenne Muscular Dystrophy"; Department of Neuroscience, Brown University, May 2007.

Cadena, Samuel M. et al.: "Administration of a soluble activin type IIB receptor promotes skeletal muscle growth independent of fiber type"; J Appl Physiol (1985). Sep. 2010; 109(3): 635-642.

Fisher, Larry W.: "Deduced Protein Sequence of Bone Small Proteoglycan I (Biglycan) Shows Homology with Proteoglycan II (Decorin) and Several Nonconnective Tissue Proteins in a Variety of Species"; The Journal of Biological Chemistry; 1989; vol. 264, No. 8, pp. 4571-4576.

Hammond, Suzan M. et al.: "PRO-051, an antisense oligonudeotide for the potential treatment of Duchenne muscular dystrophy"; Current Opinion in Molecular Therapeutics, 2010, 12:14. pp. 478-406.

Kreese, Hans et. al.: "Different Usage of the Glycosaminoglycan Attachment Sites of Biglycan", The Journal of Biological Chemistry, 2001 v. 276, No. 16, pp. 13411-13416.

Balaban, B. et al.: "Corticosteroid Treatment and Functional Improvement in Duchenne Muscular Dystrophy Long-Term Effect"; American Journal of Physical Medicine & Rehabilitation, vol. 84, No. 11, (2005), pp. 843-850.

Davies, Kay E.: "Utrophin and therapy of DMD"; PPMD Annual Conference, Jul. 13, 2007, 32 pgs.

Khan, M.A.: "Corticosteroid therapy in Duchenne muscular dystrophy". J Neurol Sci., Dec. 1, 1993, 120(1):8-14.

King, W.M. et al: "Orthopedic outcomes of long-term daily corticosteroid treatment in Duchenne muscular dystrophy". Neurology 68, May 8, 2007, pp. 1607-1613.

Krivickas, Lisa S. et al.: Single Muscle Fiber Contractile Properties in Adults With Muscular Dystrophy Treated With MYO-029; Muscle & Nerve, Jan. 2009, vol. 39, pp. 3-9.

(Continued)

*Primary Examiner* — Olga N Chernyshev
(74) *Attorney, Agent, or Firm* — DLA Piper LLP (US)

(57) ABSTRACT

The invention provides compositions and methods for treating, preventing, and diagnosing diseases or conditions associated with an abnormal level or activity of biglycan; disorders associated with an unstable cytoplasmic membrane, due, e.g., to an unstable dystrophin associated protein complex (DAPC); disorders associated with abnormal synapses or neuromuscular junctions, including those resulting from an abnormal MuSK activation or acetylcholine receptor (AChR) aggregation. Examples of diseases include Amyotrophic Lateral Sclerosis (ALS), as well as muscular dystrophies, such as Duchenne's Muscular Dystrophy, Becker's Muscular Dystrophy, neuromuscular disorders and neurological disorders.

4 Claims, 7 Drawing Sheets
Specification includes a Sequence Listing.

(56) References Cited

OTHER PUBLICATIONS

Bock et al.: "*The small proteoglycans decorin and biglycan in human articular cartilage of late-stage osteoarthritis*", Osteoarthritis and Cartilage 9 (7): 654-663. Oct. 1, 2001.
Rafii et al.: "*Biglycan Binds to a- and g-Sarcoglycan and Regulates Their Expression During Development*", Journal of Cellular Physiology; 209: 439-447. Nov. 1, 2006.
International Search Report Regarding PCT/US2013/064123.

\* cited by examiner

Capillary electrophoresis of M- and D- rhBGN.

N-linked Oligosaccharide profiling analysis of M- and D- rhBGN.

| Observed m/z | Proposed Structure | M (% Peak (Area ‡) | D (% Peak (Area ‡) |
|---|---|---|---|
| 2244.1 | (GlcNAc)4(Man)3(Gal)2(Fuc) | 0 | 49 |
| 2605.3 | (GlcNAc)4(Man)3(Gal)2(Fuc)(NeuAc) | 20 | 14 |
| 2966.4 | (GlcNAc)4(Man)3(Gal)3(Fuc)(NeuAc)2 | 24 | 11 |
| 3054.5 | (GlcNAc)5(Man)3(Gal)3(Fuc)(NeuAc) | 0 | 7 |
| 3415.6 | (GlcNAc)5(Man)3(Gal)3(Fuc)(NeuAc)2 | 15 | 10 |
| 3776.7 | (GlcNAc)5(Man)3(Gal)3(Fuc)(NeuAc)3 | 14 | 7 |
| 3865.7 | (GlcNAc)6(Man)3(Gal)4(Fuc)(NeuAc)2 | 0 | 1 |
| 4225.9/4226.8 | (GlcNAc)6(Man)3(Gal)4(Fuc)(NeuAc)3 | 26 | 1 |
| 4587.3 | (GlcNAc)6(Man)3(Gal)4(Fuc)(NeuAc)4 | 0 | 0* |

FIG. 4

SEQUENCE LISTING

<160> NUMBER OF SEQ ID NOS: 4

<210> SEQ ID NO 1
<211> LENGTH: 368
<212> TYPE: PRT
<213> ORGANISM: Homo sapiens

<400> SEQUENCE: 1

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

```
<210> SEQ ID NO 2
<211> LENGTH: 331
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 2

Asp Glu Glu Ala Xaa Gly Ala Asp Thr Xaa Gly Val Leu Asp Pro Asp
1               5                   10                  15

Ser Val Thr Pro Thr Tyr Ser Ala Met Cys Pro Phe Gly Cys His Cys
            20                  25                  30

His Leu Arg Val Val Gln Cys Ser Asp Leu Gly Leu Lys Ser Val Pro
        35                  40                  45

Lys Glu Ile Ser Pro Asp Thr Thr Leu Leu Asp Leu Gln Asn Asn Asp
50                  55                  60

Ile Ser Glu Leu Arg Lys Asp Asp Phe Lys Gly Leu Gln His Leu Tyr
65                  70                  75                  80

Ala Leu Val Leu Val Asn Asn Lys Ile Ser Lys Ile His Glu Lys Ala
                85                  90                  95

Phe Ser Pro Leu Arg Lys Leu Gln Lys Leu Tyr Ile Ser Lys Asn His
            100                 105                 110

Leu Val Glu Ile Pro Pro Asn Leu Pro Ser Ser Leu Val Glu Leu Arg
        115                 120                 125

Ile His Asp Asn Arg Ile Arg Lys Val Pro Lys Gly Val Phe Ser Gly
130                 135                 140

Leu Arg Asn Met Asn Cys Ile Glu Met Gly Gly Asn Pro Leu Glu Asn
145                 150                 155                 160

Ser Gly Phe Glu Pro Gly Ala Phe Asp Gly Leu Lys Leu Asn Tyr Leu
                165                 170                 175

Arg Ile Ser Glu Ala Lys Leu Thr Gly Ile Pro Lys Asp Leu Pro Glu
            180                 185                 190

Thr Leu Asn Glu Leu His Leu Asp His Asn Lys Ile Gln Ala Ile Glu
        195                 200                 205

Leu Glu Asp Leu Leu Arg Tyr Ser Lys Leu Tyr Arg Leu Gly Leu Gly
210                 215                 220

His Asn Gln Ile Arg Met Ile Glu Asn Gly Ser Leu Ser Phe Leu Pro
225                 230                 235                 240

Thr Leu Arg Glu Leu His Leu Asp Asn Asn Lys Leu Ala Arg Val Pro
                245                 250                 255

Ser Gly Leu Pro Asp Leu Lys Leu Leu Gln Val Val Tyr Leu His Ser
            260                 265                 270

Asn Asn Ile Thr Lys Val Gly Val Asn Asp Phe Cys Pro Met Gly Phe
        275                 280                 285

Gly Val Lys Arg Ala Tyr Tyr Asn Gly Ile Ser Leu Phe Asn Asn Pro
290                 295                 300

Val Pro Tyr Trp Glu Val Gln Pro Ala Thr Phe Arg Cys Val Thr Asp
305                 310                 315                 320

Arg Leu Ala Ile Gln Phe Gly Asn Tyr Lys Lys
```

<210> SEQ ID NO 3
<211> LENGTH: 331
<212> TYPE: PRT
<213> ORGANISM: Artificial Sequence
<220> FEATURE:
<223> OTHER INFORMATION: Synthetic Construct

<400> SEQUENCE: 3

```
Asp Glu Glu Ala Ala Gly Ala Asp Thr Ala Gly Val Leu Asp Pro Asp
1               5                   10                  15

Ser Val Thr Pro Thr Tyr Ser Ala Met Cys Pro Phe Gly Cys His Cys
            20                  25                  30

His Leu Arg Val Val Gln Cys Ser Asp Leu Gly Leu Lys Ser Val Pro
        35                  40                  45

Lys Glu Ile Ser Pro Asp Thr Thr Leu Leu Asp Leu Gln Asn Asn Asp
    50                  55                  60

Ile Ser Glu Leu Arg Lys Asp Asp Phe Lys Gly Leu Gln His Leu Tyr
65                  70                  75                  80

Ala Leu Val Leu Val Asn Asn Lys Ile Ser Lys Ile His Glu Lys Ala
                85                  90                  95

Phe Ser Pro Leu Arg Lys Leu Gln Lys Leu Tyr Ile Ser Lys Asn His
            100                 105                 110

Leu Val Glu Ile Pro Pro Asn Leu Pro Ser Ser Leu Val Glu Leu Arg
        115                 120                 125

Ile His Asp Asn Arg Ile Arg Lys Val Pro Lys Gly Val Phe Ser Gly
    130                 135                 140

Leu Arg Asn Met Asn Cys Ile Glu Met Gly Gly Asn Pro Leu Glu Asn
145                 150                 155                 160

Ser Gly Phe Glu Pro Gly Ala Phe Asp Gly Leu Lys Leu Asn Tyr Leu
                165                 170                 175

Arg Ile Ser Glu Ala Lys Leu Thr Gly Ile Pro Lys Asp Leu Pro Glu
            180                 185                 190

Thr Leu Asn Glu Leu His Leu Asp His Asn Lys Ile Gln Ala Ile Glu
        195                 200                 205

Leu Glu Asp Leu Leu Arg Tyr Ser Lys Leu Tyr Arg Leu Gly Leu Gly
    210                 215                 220

His Asn Gln Ile Arg Met Ile Glu Asn Gly Ser Leu Ser Phe Leu Pro
225                 230                 235                 240

Thr Leu Arg Glu Leu His Leu Asp Asn Asn Lys Leu Ala Arg Val Pro
                245                 250                 255

Ser Gly Leu Pro Asp Leu Lys Leu Leu Gln Val Val Tyr Leu His Ser
            260                 265                 270

Asn Asn Ile Thr Lys Val Gly Val Asn Asp Phe Cys Pro Met Gly Phe
        275                 280                 285

Gly Val Lys Arg Ala Tyr Tyr Asn Gly Ile Ser Leu Phe Asn Asn Pro
    290                 295                 300

Val Pro Tyr Trp Glu Val Gln Pro Ala Thr Phe Arg Cys Val Thr Asp
305                 310                 315                 320

Arg Leu Ala Ile Gln Phe Gly Asn Tyr Lys Lys
                325                 330
```

<210> SEQ ID NO 4

```
<211> LENGTH: 368
<212> TYPE: PRT
<213> ORGANISM: Homo sapiens

<400> SEQUENCE: 4

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Ala Ala Gly Ala Asp Thr Ala Gly
        35                  40                  45

Val Leu Asp Pro Asp Ser Val Thr Pro Thr Tyr Ser Ala Met Cys Pro
50                  55                      60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
                100                 105                 110

Leu Gln His Leu Tyr Ala Leu Val Leu Val Asn Asn Lys Ile Ser Lys
            115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

BIGLYCAN VARIANT POLYPEPTIDES AND METHODS OF USE

CROSS REFERENCE TO RELATED APPLICATIONS

This application claims benefit of priority under 35 U.S.C. § 119(e) of U.S. Ser. No. 61/712,177, filed Oct. 10, 2012, the entire contents of which are incorporated herein by reference in its entirety.

GOVERNMENT RIGHTS

This invention was made with government support under grants UO1NS064295 (NIH), R21AR055878 (NIAM), and HD023924 (DHHS) awarded by the National Institutes of Health. The government has certain rights in the invention.

INCORPORATION OF SEQUENCE LISTING

The material in the accompanying Sequence Listing is hereby incorporated by reference into this application. The accompanying sequence listing text file, name TIVOR1100_1_Sequence_Listing_ST25, was created on Oct. 8, 2013 and is 10 KB. The file can be assessed using Microsoft Word on a computer that uses Windows OS.

BACKGROUND OF THE INVENTION

Field of Use

The present invention relates generally to proteoglycans, and more specifically to biglycan variants and use of such variants in the treatment of disease.

Background Information

Biglycan is a 37 kd extracellular matrix protein. In muscle, biglycan exists in two glycoforms: a proteoglycan that bears two glucosaminoglycan (GAG) side chains and a non-glycanated form that lacks GAG chains. Both forms contain N-linked carbohydrates at two sites. Previous work showed that in mdx mice the recombinant non-glycanated version is effective in: 1) recruiting utrophin and other DAPC components to the muscle membrane; 2) improving muscle health; and 3) improving muscle function.

Biglycan is an extracellular matrix component of many parts of the skeleton including bone, cartilage, tendon, teeth and muscle. Biglycan is predominantly expressed as a proteoglycan, but a mature form lacking GAG side chains ('nonglycanated') has recently been shown to have specific functions in muscle, synapses and Wnt signaling in bone. The biglycan gene is on the X (and not Y) chromosome and is dysregulated in Turner (XO) and Kleinfelter's Syndromes (supernumery X) diseases, characterized by short and tall stature respectively. Biglycan deficient mice have shorter bones as well as lower bone mass (ostepenia/osteoporosis), another notable feature observed in Turner Syndrome. The mechanisms underlying the thinner and weaker bones produced without biglycan have been studied in detail and point to the fact that biglycan modulates multiple pathways critical to skeletal metabolism.

While biglycan is not needed for development of the musculoskeletal system, it is required for the maintenance of its integrity. In adult bone turnover is regulated by a fine balance between bone formation by osteoblasts and bone resorption by osteoclasts. In the absence of biglycan, there is decreased bone formation due to defects in the maturation of osteogenic precursors that form bone. Bone Morphogenic Protein 2/4 (BMP-2/4), a well-known inducer of bone formation, is currently being used therapeutically to aid bone repair. Bone-derived cells depleted of biglycan have less BMP-2/4 binding and subsequently less osteogenic differentiation. It is logical to conclude that biglycan could be a prime candidate to enhance BMP-2/4 function in situations where it is commonly used such as in bone regeneration and repair after fracture or trauma.

Mice lacking biglycan also display pathologies typically associated with skeletal aging. Specifically, by three months of age, hallmark signs of osteoarthritis (OA) are evident in the mutant mice, including fissures, cell clustering and loss of the smooth articular cartilage surface on the joints. The OA is detected in all weight bearing joints as well as in the temporomandibular joint of the jaw. The effects of biglycan loss are exacerbated by depletion of the related small leucine-rich proteoglycan fibromodulin (Bgn–/0; Fmod–/– DKO). Molecular studies point to the abnormal sequestration of the potent growth factor TGF-beta in the combined absence of biglycan and fibromodulin causing it to be "unleashed" and subsequently overactive. The uncontrolled stimulation of TGF-beta in this context leads to hyperproliferation, premature differentiation of cartilage derived cells, MMP induction and, ultimately, loss of the condyle tissue integrity.

Biglycan can also control the fate of skeletal stem cells by modulating the extracellular niche. This function was demonstrated in ECM-rich tendon tissue that harbors a cell population with stem cell features including clonogenicity, multipotency and regenerative capabilities. The combined removal of biglycan and fibromodulin caused tendon stem/ progenitor cells to be hypersensitive to BMP-2. Instead of differentiating into tendon, these progenitors form multiple ectopic bones within the tendons that affect the gait of the mice. Biglycan also controls other factors critical to bone in addition to TGF-beta and BMP-2/4. In humans, a mutation in the extracellular domain of the key Wnt signaling molecule LRP-6 (R611C) causes elevated cholesterol and osteopenia. Notably, exogenous application of non-glycanated biglycan repaired the defective Wnt signaling in cells expressing mutant LRP-6. Thus, biglycan could potentially ameliorate pathologies caused by defective Wnt signaling. Taken together these findings underscore the importance of biglycan in modulating several key growth factor-mediated signaling pathways that regulate skeletal tissue architecture and function.

Biglycan also plays a role in organizing membrane architecture and function in muscle and at synapses. Muscle membranes are highly specialized to transmit force, protect the cell from contraction-induced damage and orchestrate signaling pathways required for normal function. The dystrophin- and utrophin-membrane glycoprotein complexes (DGC and UGC, respectively) link the cytoskeleton to the extracellular matrix and serve as a scaffold for signaling molecules in adult (DGC) and immature (UGC) muscle. Biglycan binds to three shared components of these complexes: the extracellular peripheral membrane protein alpha-dystroglycan and the transmembrane proteins alpha- and beta-sarcoglycan. Genetic studies show that biglycan regulates the expression of utrophin, the two sarcoglycans and an intracellular membrane-associated signaling complex comprised of dystrobrevin, syntrophins and nNOS (neuronal nitric oxide synthase) in immature muscle. Notably, dosing mice with recombinant non-glycanated biglycan (rNG-BGN) can restore the expression of several of these components to the membrane.

The role of biglycan in binding and regulating several components of DGC and UGC, coupled with the ability to deliver rNG-BGN systemically, suggested that biglycan could be a therapeutic for Duchenne Muscular Dystrophy (DMD). DMD is the most common form of muscular dystrophy and results from mutations in dystrophin—a large intracellular protein that links the actin cytoskeleton to the membrane and anchors the DGC. Notably, utrophin upregulation can compensate for dystrophin loss in mouse models of DMD (mdx; Davies). Systemically-delivered rNG-BGN recruits utrophin to the membrane and improves muscle health and function in mdx mice. The efficacy of the non-glycanated form (i.e. lacking GAG side chains) in this therapeutic approach is most likely based on two reasons. First, this form can be readily manufactured in a homogeneous form. Second, the glyconated form of biglycan, proteoglycan (PG), is proinflammatory, but the non-glycanated (core) is not. A non-glycanated form of biglycan is currently in preclinical development for DMD.

Biglycan is also important for synapse stabilization. In biglycan-deficient mice, neuromuscular junctions form normally but then they become unstable about three weeks after birth. The mechanism of biglycan action at the synapses is likely to involve MuSK, a receptor tyrosine kinase that is the master regulator of synapse differentiation and maintenance. Biglycan binds to MuSK and regulates its expression in vivo. Notably, synaptic loss is one of the earliest abnormalities observed in almost all neurodegenerative diseases, including ALS (amyotrophic lateral sclerosis) and SMA (spinal muscular atrophy). Treatments that promote neuromuscular junction stability could prolong function and potentially survival in these devastating motor neuron diseases.

SUMMARY OF THE INVENTION

The invention is based on the discovery of a biglycan variant termed T2-rhBGN (T2 recombinant human biglycan). In this molecule the two sites of GAG addition have been mutated to alanine. Enzymatic and carbohydrate analysis showed that this form completely lacks GAG side chains. Stable clonal cell lines expressing T2-rhBGN have been derived from CHO and HEK 293 hosts. Data from three of these lines (CHO 57, CHO 171, HEK 293) are included herein.

Biglycan plays important roles in the musculoskeletal system. The fact that non-glycanated forms of biglycan are effective in ameliorating muscle defects and that it can be administered systemically makes it particularly amenable for tissue and cell therapy. Taken together, it is reasonable to conclude that biglycan holds promise as a novel therapeutic for numerous musculoskeletal diseases including low bone mass, osteoarthritis, ectopic bone formation and muscular dystrophy.

Accordingly, in one aspect, the present invention provides an isolated biglycan variant polypeptide lacking glycosaminoglycan (GAG) side chains. In various embodiments, the variant polypeptide potentiates agrin-induced AChR clustering and is the M form of the molecule. In one embodiment the variant polypeptide includes an amino acid sequence which is at least about 90%, 95%, 96%, 97%, 98% or 99% identical to SEQ ID NO: 1, or portion thereof, includes a mutation at amino acid residue 42 or 47, or combination thereof. In some embodiments, the mutation at amino acid residue 42 or 47 is substitution with an alanine. In some embodiments, the variant polypeptide includes an amino acid sequence as set forth in amino acid residues 38-48 of SEQ ID NO: 1. In some embodiments, the variant polypeptide includes an amino acid sequence as set forth in amino acid residues 38-80 of SEQ ID NO: 1.

In another aspect, the invention provides an isolated nucleic acid molecule encoding the variant polypeptide of the present invention.

In another aspect, the invention provides an expression cassette including the nucleic acid encoding the variant polypeptide of the present invention.

In another aspect, the invention provides a vector including the expression cassette of the present invention.

In another aspect, the invention provides a pharmaceutical composition.

In one embodiment, the pharmaceutical composition includes the variant polypeptide of the present invention and a pharmaceutically acceptable carrier. In another embodiment, the pharmaceutical composition includes a nucleic acid molecule encoding the variant polypeptide of the present invention and a pharmaceutically acceptable carrier.

In yet another aspect, the invention provides a method of preventing or treating a disorder in the subject. The method includes administering to the subject a composition including the variant polypeptide of the present invention or a pharmaceutical composition including such a peptide as described herein.

In another aspect, the invention provides a method for determining whether a subject has or is at risk of developing a disorder. The method includes: a) determining a level or activity of the variant polypeptide of the present invention in a sample from the subject; and b) comparing the level or activity of the variant polypeptide to that of a corresponding or known sample, wherein an increase or decrease the level or activity of the variant polypeptide as compared to that of the corresponding or known sample is indicative of having or developing the disorder, thereby determining whether the subject has or is at risk of developing the disorder. In various embodiments, the method further includes administering to the subject a composition including the variant polypeptide of the present invention or pharmaceutical composition as described herein.

In various embodiments, disorders include muscular, neuromuscular and neurological disorders. Such disorders include those associated with an abnormal dystrophin-associated protein complex (DAPC) and those disorders that are characterized by an abnormal neuromuscular junction or synapse in the subject. In some embodiments, the disorder is muscular dystrophy, such as Duchenne's Muscular Dystrophy, Becker's Muscular Dystrophy, Congenital Muscular Dystrophy, Lamb-girdle Muscular Dystrophy, and mytonic dystrophy, or the disorder is low bone mass, osteoarthritis, or ectopic bone formation. In other embodiments, the disorder could be other neurodegenerative disorders such as Amyotrophic Lateral Sclerosis (ALS). In other embodiments, the disorder could be other muscular disorders such as congestive heart failure.

200 column equilibrated with 1.0M NaCl, 20 mM Tris, pH 8.0. a) First SEC: HIC pool resolved into two discrete, partially overlapping peaks that eluted at ~18.7 (D) and 20.4 ml (M). b) Fractions corresponding to M and D were re-analyzed on the size exclusion column. The elution profiles (overlaid) show a clear separation of the M and D forms and there was little exchange between them.

Figure 3A:
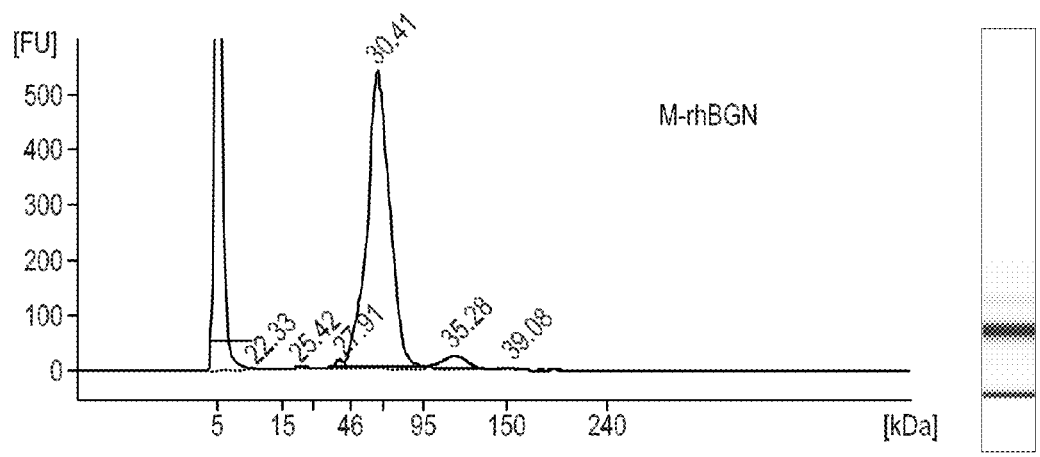
Figure 3B:
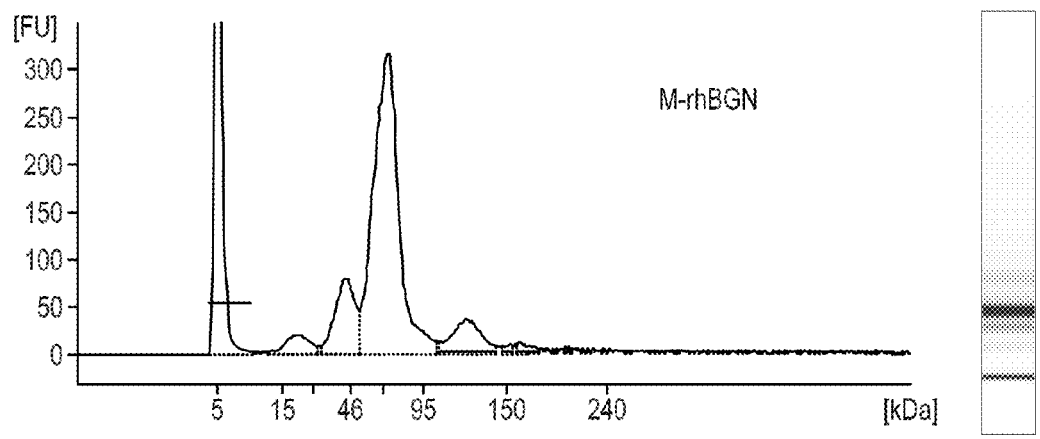

FIG. 3a-b. Capillary electrophoresis of M- and D-rhBGN. M- and D-rhBGN were purified from CHO Clone 57 by size exclusion chromatography. M and D were analyzed by capillary electrophoresis using an Agilent Bioanalyzer 2100™ and Agilent Protein 80™ assay kit. The apparent molecular weight and mobility of D-rhBGN were greater than that of M-rhBGN, indicating differential posttranslational modification of the two forms.

FIG. 4. N-linked Oligosaccharide profiling analysis of M- and D-rhBGN. M- and D-rhBGN were purified from CHO Clone 57 by size exclusion chromatography. N-glycans were cleaved from the samples, purified and analyzed by MALDI/TOF-TOF. The percentages of each glycan were calculated for each sample. M and D forms showed varying amounts of complex-type glycans, branching and sialic acid.

Figure 5:
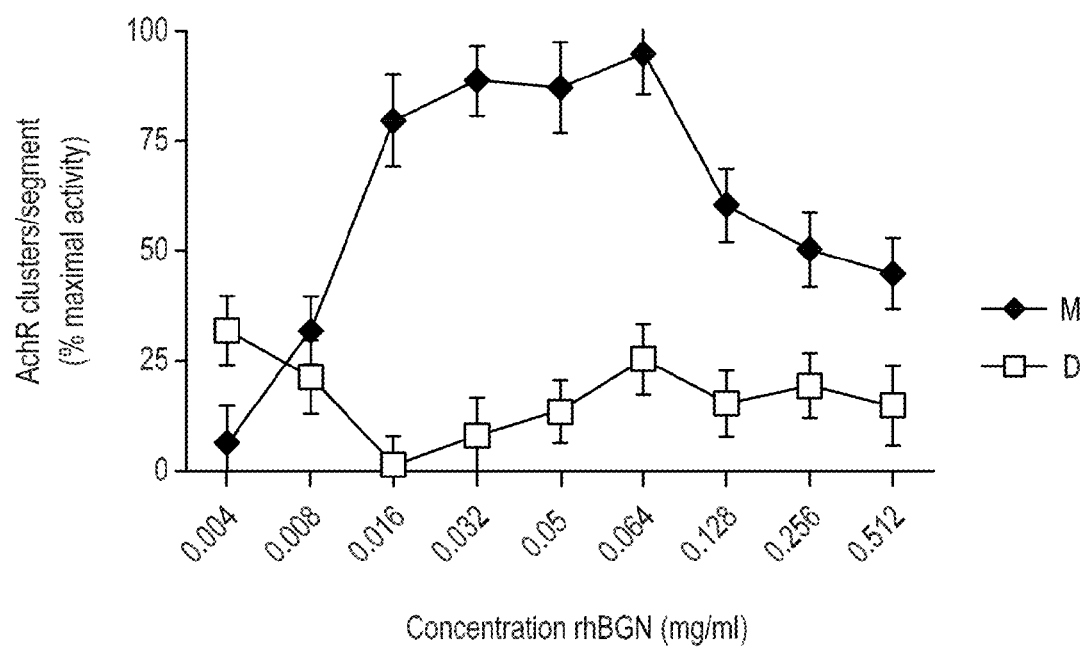

FIG. 5. Bioactivity of M- and D-rhBGN. M- and D-rhBGN were purified from CHO Clone 171 by size exclusion chromatography and tested for bioactivity using an AChR clustering assay. Note the robust and broad dose-response observed with M-rhBGN and the uniformly low activity at all concentrations of D-rhBGN.

Figure 6:
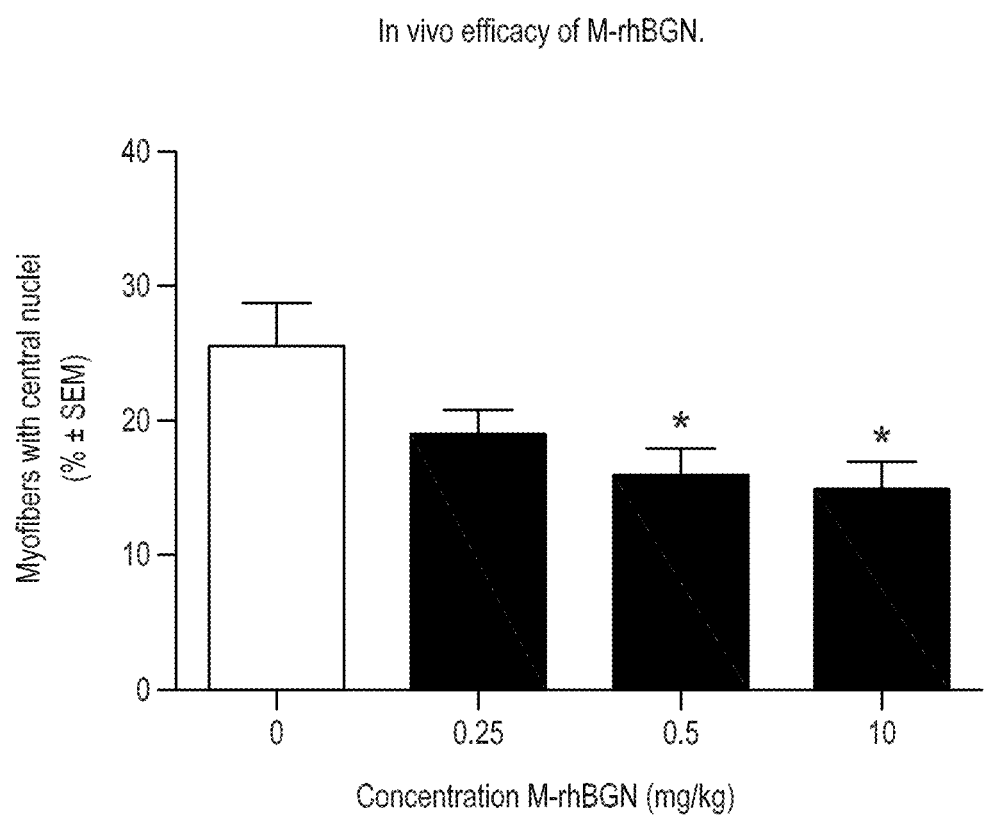

FIG. 6. In vivo efficacy of M-rhBGN. M-rhBGN was purified from HEK-293 Clone 2 by size exclusion chromatography. Male mdx mice were IP injected at P18 and P25 with the indicated doses of M-rhBGN or vehicle. Diaphragm muscles were harvested at P32 and myofibers with central nuclei were scored. M-rhBGN reduced the percentage of myofibers with central nuclei (*$p<0.05$, 1-way ANOVA analysis with post-hoc Dunnett's Multiple Comparison, n=7-10 animals/group). There was a statistically significant response across a 20-fold range (0.5-10 mg/kg).

Figure 7A:
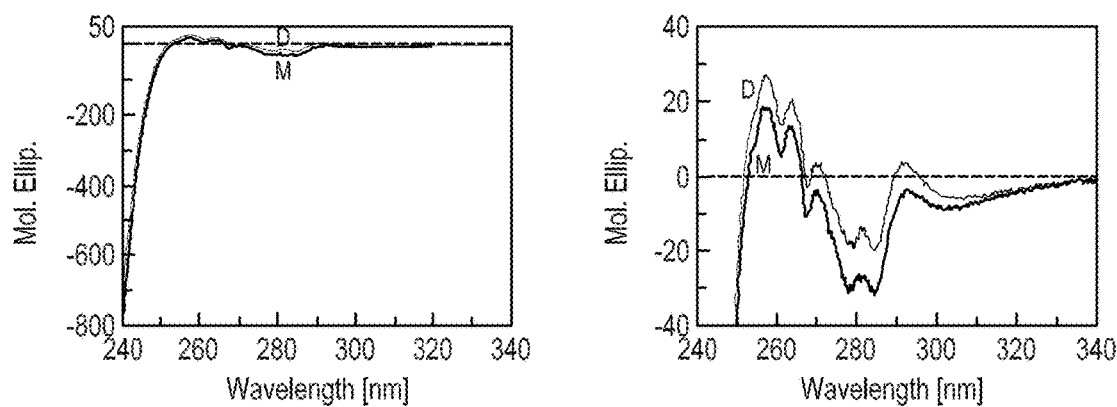
Figure 7B:
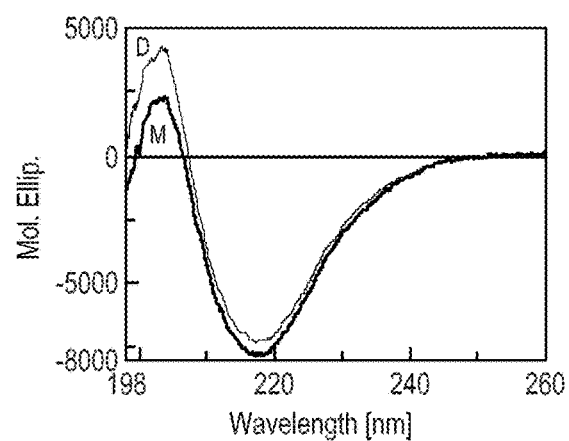

FIG. 7. Near and Far UV CD of M- and D-rhBGN. a) Near UV CD spectra of M-(black) and D-rhBGN (gray). There is a difference between M and D, as seen in the expanded scale (right panel), with D spectrum shifted upward. b) Far UV CD spectra of M-(black) and D-rhBGN (gray). There is a difference in the spectra of M and D, indicating the different forms have different structures.

BRIEF DESCRIPTION OF THE INVENTION

The invention is based on the discovery of a biglycan variant termed T2-rhBGN (T2 recombinant human biglycan) in which sites of GAG addition have been mutated thereby eliminating addition of GAG side chains to the variant. Such variants are useful in various therapeutic and diagnostic application. As such, in one aspect, the invention provides biglycan therapeutics for use in maintaining the integrity of plasma cell membranes, in particular, biglycan therapeutics which stabilize dystrophin associated protein complexes (DAPC) in these membranes, thereby preventing the disintegration of the membranes. The invention also provides biglycan therapeutics which stimulate neuromuscular junction formation, such as by stimulating postsynaptic membrane differentiation, and more generally compounds which stimulate synapse formation.

Preferred therapeutics of the invention have one or more biological activities of biglycan, in addition to, or instead of, being able to bind one or more components of the DAPC and/or MuSK. For example, a therapeutic of the invention can stimulate neuromuscular junction formation, in particular, postsynaptic membrane differentiation, including inducing aggregation of AChRs and/or stimulating or stimulating agrin-induced tyrosine phorphorylation of MusK.

The therapeutics of the invention can be a protein or derivative thereof, in particular a biglycan variant polypeptide as described herein. The variant of the present invention has a mutated sequence which eliminates addition of GAG side chains.

In a preferred embodiment, the variant of the invention is the M form proteoglycan having a molecular weight from about 40 kDa to about 44 kDa, as determined, e.g., by migration on an SDS acrylamide gel. In the preferred embodiment, the "M form" is generally considered monomeric, but is not required to be monomeric. Fragments or portions of these proteoglycans are also within the scope of the invention. While not wanting to be bound by a particular theory it is believed that the D form of biglycan negatively affects the M form (when in a mixture). In the preferred embodiment, the "D form" is generally dimeric, but is not required to be dimeric. It merely negatively affects the M form.

The proteoglycan of the invention is a member of the family of small leucine-rich proteoglycans (SLRP), also referred to as "nonaggreagating or small dermatan-sulfate proteoglycans because of their inability to interact with hyaluronan, or because of their type of glycosaminoglycans, respectively. SLRPs are organized into three classes based on their protein and genomic organization. All SLRPs are characterized by a central domain containing leucine rich repeats (LRR) flanked at either side by small cysteine clusters. The SLRPs are described, e.g., in Iozzo et al. (1998) Ann. Rev. Biochem. 67:609, specifically incorporated herein by reference.

SLRP protein cores range from about 35-45 kD with one or two GAG chains attached at the extreme N-terminus. The general structure of the SLRP protein core consists of a tandem array of 6-10 leucine-rich repeats (LRR) flanked by domains with conserved, disulfide-bonded cysteines. Depending upon the extent of glycosylation and number of GAG chains, the native molecular weight ranges from .about.100-250 kD. On the basis of their sequence homology, Iozzo, supra, has proposed that SLRPs be grouped into three classes consisting of: 1) biglycan and decorin; 2) fibromodulin, lumican, keratocan, PREPLP, and osteoadherin; and 3) epiphycan and osteoglycin. The most compelling feature of the SLRP protein core are the LRRs. Such repeats (24aa each in the SLRPs) mediate protein-protein interactions in a wide variety of intracellular, transmembrane, and extracellular contexts (Kobe & Deisenhofer, (1994) Trends Biochem. Sci. 19: 415-21). The neurotrophin binding site on trkB, for example, is an LRR (Windisch et al., (1995) Biochemistry 34: 11256-63). The repeats are thought to have a general structure of an .alpha.-helix followed by beta-sheet in an anti-parallel array, although sequence analysis has suggested that this order might be reversed in the SLRPs (Hocking et al., (1998) Matrix Biol. 17: 1-19). It is likely that the conserved residues of each repeat dictate their secondary structure, while the intervening amino acids determine specificity of ligand binding.

Preferred SLRPs for use in the invention include Class I SLRPs, such as biglycan. Nucleotide and amino acid sequences of biglycan genes and proteins from various species are publically available, such as in GenBank. For example, human biglycan can be found under GenBank Accession No. J04599 (human hPGI encoding bone small proteoglycan I (biglycan), described in Fisher et al. (1989)

J. Biol. Chem. 264: 4571) and M65154; cow biglycan can be found under GenBank Accession No. L07953; rat biglycan can be found under GenBank Accession No. U17834, mouse biglycan can be found under GenBank Accession No. L20276 and X53928; ovis biglycan can be found under GenBank Accession No. AF034842.

Typically, biglycan has two glycosaminoglycan (GAG) chains, respectively. Their composition is tissue specific and can be regulated at a number of levels (Hocking et al., (1998) Matrix Biol 17: 1-19). For example, the biglycan GAG from skin and cartilage is predominantly dermatan sulfate, while biglycan synthesized in bone is a chondroitin sulfate proteoglycan. Heparan sulfate side chains have not been reported. Both the protein core and the cell type contribute to the distinct glycosylation of these SLRPs.

However, as discussed herein, the proteoglycan of the present invention has a mutated sequence which eliminates addition of GAG side chains. Portions and fragments of the proteoglycans of the invention are also within the scope of the invention. A portion is typically at least five, 10, 15, or 20 amino acids long. Preferred portions are those which are sufficient for exerting a biological activity, such as interacting with a DAPC component. Portions can comprise or consist of one or more specific domain of a protein. Domains of biglycan include two cysteine-rich regions (included in the N- and C-terminal 40-50 amino acids of mature biglycan) and leucine-rich repeats (LRRs). The "LRR region" refers to the region of biglycan containing the repeats, and consists essentially of amino acids 81-314. Each individual repeat is referred to herein as an "LRR." LRRs are believed to mediate protein: protein interactions and may thus be sufficient for stabilizing DAPCs and postsynaptic membranes.

A preferred biglycan of the invention consists of a portion of biglycan that is capable of binding to a sarcoglycan. It has been shown that the α-sarcoglycan binding domain of human biglycan is located in the N-terminal domain of the mature biglycan protein, i.e., amino acids 38-80, and more specifically, amino acids 38-58 of SEQ ID NO: 1. The GAG chains are not necessary for binding to α-sarcgoglycan. It has also been shown that the C-terminal cysteine-rich domain mediates interaction with γ-sarcoglycan. Accordingly, preferred biglycans of the invention include portions of biglycan consisting of the N-terminal or the C-terminal cysteine-rich domain, i.e., amino acids 38-48, 38-80 and 315-368 of SEQ ID NO: 1. Combinations of certain domains of biglycan are also within the scope of the invention.

Preferred fragments consist of at least about 30 amino acids, at least about 40 amino acids, 50, 60, 70, 80, 90, 100, 150, or 200 amino acids. Short portions of the proteoglycans of the invention are termed "mini-proteoglycan of the invention." For example, a biglycan core fragment of about 20, 30 or 40 amino acids is referred to as a "mini-biglycan."

Human biglycan consists of 368 amino acids (SEQ ID NO: 1), of which amino acids 1-19 constitute a signal peptide (GenBank Accession No. NP001702 and Fisher et al., supra). Thus biglycan without a signal peptide consists of amino acids 20-368 of SEQ ID NO: 1. The mature biglycan protein consists of amino acids 38-368 of SEQ ID NO: 1, since amino acids 1-37, being a pre-propeptide, are cleaved during processing. Amino acids 38-80 correspond to the N-terminal cysteine-rich region. About amino acids 81-314 corresponds to the leucine rich repeat region, containing 10 repeats of about 24 or 23 amino acids.

A proteoglycan of the present invention is a variant biglycan polypeptide having a mutated sequence with reference to SEQ ID NO: 1 or SEQ ID NO: 2. In one embodiment, the variant includes mutations at amino acid residues 42 and 47 (corresponding to amino acid positions 5 and 10 of SEQ ID NO: 2) which eliminate GAG side chains. In one embodiment, the variant has the amino acid sequence of SEQ ID NO: 2, wherein either or both amino acids 5 and 10 are any amino acid other than serine (wild type). In one embodiment, the variant has the amino acid sequence of SEQ ID NO: 3 in which amino acids 5 and 10 are alanine.

Preferred proteoglycans of the invention are encoded by nucleotide sequences which are at least about 70%, preferably at least about 80%, even more preferably at least about 85%, at least about 90%, at least about 95%, at least about 98%, and even more preferably at least about 99% identical to the nucleotide sequence of an SLRP, e.g., biglycan, or portion thereof.

Preferred nucleic acids of the invention include those encoding a polypeptide comprising an amino acid sequence which is at least about 70%, preferably at least about 80%, even more preferably at least about 85%, at least about 90%, at least about 95%, at least about 98%, and even more preferably at least about 99% identical to the nucleotide sequence of an SLRP, e.g., biglycan, or portion thereof. In one embodiment, the nucleic acid encodes a polypeptide containing all or a fragment of SEQ ID NO: 1.

Methods for preparing compounds of the invention are well known in the art. For a compound of the invention which is a protein or a derivative thereof, the compound can be isolated from a tissue or the compound can be recombinantly or synthetically produced. Isolation of the protein from a tissue is described in the Examples. The proteins or proteoglycans of the invention isolated from tissue are preferably at least about 70%, preferably at least about 80%, at least about 85%, at least about 90%, at least about 95%, at least about 98% and most preferably, at least about 99% pure. Accordingly, preferred compounds contain less than about 1%, and even more preferably less than about 0.1% of material from which the compound was extracted.

The protein of the invention can also be produced recombinantly, according to methods well known in the art. Typically, a gene encoding the protein is inserted into a plasmid or vector, and the resulting construct is then transfected into appropriate cells, in which the protein is then expressed, and from which the protein is ultimately purified.

Accordingly, the present invention further pertains to methods of producing the subject proteins. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a protein of the present invention can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIPS, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 on, and in S. cerevisiae due to the replication determinant of the yeast 2 micron plasmid. In addition, drug resistance markers such as ampicillin can be used.

The protein can be produced either in eukaryotic cells, e.g., mammalian cells, yeast cells, insect cell (baculovirus system) or in prokaryotic cells. When biglycan is used in the context of muscle cells, it is preferable to produce biglycan in muscle cells, e.g., C2 muscle cells.

Alternatively, a protein core of a proteoglycan can be produced in a prokaryote, which results in a protein without glucose side chains.

Immortalized cell lines, e.g., muscle cell lines, such as biglycan negative cell lines, can be obtained as described in Jat et al., PNAS (1991) 88: 5096-100; Noble et al., (1992) Brain Pathology 2: 39-46. In one embodiment, a H-2K$^b$/tsA58 transgenic mouse is used. This mouse is a heterozygote harboring a thermolabile immortalizing gene (the tsA58 mutant of SV40 large T antigen) under the control of an interferon-inducible promoter (this mouse is available at Charles River). When cells containing this gene are cultured, they proliferate indefinitely at 33 C. in the presence of interferon. However, when the temperature is raised to 39 C. (at which temperature the tsA58 antigen is non-functional) and interferon is removed, the cells cease dividing.

This method has been used for growing a wide variety of cell types, including astrocytes, osteoclasts, trabecular network, and colon epithelial cells (Chambers et al., (1993) PNAS 90: 5578-82; Groves et al., (1993) Dev. Biol. 159: 87-104; Whitehead et al., (1993) PNAS 90: 587-91; Noble et al., (1995) Transgenic Res. 4: 215-25; Tamm et al., (1999) Invest. Ophtamol. Vis. Sci. 40: 1392-403. This technique is well suited for the production of muscle cell lines. For example, in one study alone 65 separate muscle cell lines were derived from animals ranging in age from neonates to four weeks (Morgan et al., (1994) Dev. Biol. 162 486-98). These lines were maintained for upwards of 80 generations. Remarkably, they not only formed myotubes when shifted to non-permissive conditions in culture, but also formed muscle when implanted into host mice. The H-2K$^b$/tsA58 transgenic method was also used by D. Glass and colleagues to produce a MuSK$^{-/-}$ muscle cell line (Sugiyama et al., (1997) J. Cell Biol. 139: 181-91).

To produce conditionally immortalized cell lines, mice having a specific mutation, e.g., a deficiency in biglycan or MuSK, can be crossed with heterozygote H-2K$^b$/tsA58 transgenic mice. The crosses are straightforward since only one copy of the gene is required for full activity. Muscle cells from neonatal animals can then be plated out and grown under permissive conditions (33 C with interferon). Proliferating cells can then be cloned and samples from each line shifted to the non-permissive temperature and tested for their ability to form myotubes. Wild type; decorin$^{-/-}$; biglycan$^{-/o}$; and decorin$^{-/-}$ biglycan$^{-/o}$ cell lines are examples of cell lines which can be obtained using this technique.

Although the preferred method for treating subjects with a biglycan is by administration of the biglycan to the subject (based at least on the efficiency of biglycan when added to cell cultures), the proteoglycans of the invention can also be produced in a subject, by gene therapy techniques. Thus, e.g., a subject can receive an injection in a muscle (e.g., where the subject has a muscle dystrophy) of a vector encoding a protein or proteoglycan of the invention, such that the vector is capable of entering muscle cells and being expressed therein. Alternatively, the vector can be a viral vector, which is provided with the viral capsid and the virus infects the cells, e.g., muscle cells and thereby deliver the vector. Methods and vectors for gene therapy are well known in the art. Illustrative methods are set forth below.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pFIEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the -gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals.

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054-3057).

The gene encoding the proteoglycan of the invention can be under the control of a constitutive, or inducible promoter. These are well known in the art.

Methods for determining whether a compound has a biological activity of a biglycan protein are described. A biological activity of a biglycan protein is intended to refer to one or more of: the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan; phosphorylation of α-sarcoglycan; binding to MuSK; stimulating the formation of neuromuscular junctions, such as by stimulating postsynaptic differentiation; stimulating AChR aggregation; stimulation of MuSK phosphorylation and potentiation of agrin-induced MuSK phosphorylation. Such methods can further be adapted for screening libraries of compounds for identifying compounds having one or more of the above-described activities.

Breakdown of cytoplasmic membranes, e.g., the presence of "leaky membranes" can be determined by assays which measure the release of creatine kinase or the absorption of Evans Blue dye, as described, e.g., in Tinsley et al. (1996) Nature 384: 349 and Straub et al. (1997) J. Cell Biol. 139: 375).

The compounds of the invention can also be tested in a variety of animal models, in particular the mdx mice, which are dystrophin negative.

Methods of Treatment

The invention provides therapeutic and prophylactic methods of treatment of disorders including muscular, neuromuscular, and neurological disorders. Therapeutic methods are intended to eliminate or at least reduce at least one symptom of a disease or disorder, and preferably cure the disease or disorder. Prophylactic methods include those intended to prevent the appearance of a disease or disorder, i.e., a method which is intended to combat the appearance of the disease or disorder.

Furthermore, since DAPCs are also found on other cell types, the invention also provides methods for treating diseases associated with any abnormal DAPC. For example, DAPC are present in the brain, and since, in addition, agrin has been found in senile plaques in patients with Alzheimers's disease, neurological diseases can also be treated or prevented according to the methods of the invention. A further indication that neurological disorders can be treated or prevented according to the methods described herein is based on the observation that patients with muscular dystrophy often also suffer from peripheral and central nervous system disorder. Accordingly, about one third of patients with Duchenne Muscular Dystrophy have a mental affliction, in particular, mental retardation. Thus, dystrophin, and hence, DAPCs, are believed to play a role in the nervous system.

Patients with Duchenne's Muscular Dystrophy also have diaphragm problems, indicating a role for dystrophin, and possibly DAPCs in diaphragms. Thus, therapeutics of the invention would also find an application in disorders associated with diaphragm abnormalities.

It should be noted that diseases that can be treated or prevented include not only those in which biglycan is abnormal, but more generally any disease or condition that is associated with a defect that can be improved or cured by biglycan. In particular, diseases that are characterized by a defect or an abnormality in any component of the DAPC or component associated therewith, thereby resulting, e.g., in an unstable plasma membrane, can be treated or prevented according to the methods of the invention, provided that the proteoglycan of the invention can at least partially cure the defect resulting from the deficient component. In particular, diseases that can be treated according to the method of the invention include any disease associated with an unstable DAPC, which can be rendered more stable by the presence of a proteoglycan of the invention.

Exemplary Diseases and Disorders: Diseases or disorders that are characterized by a destabilization or improper organization of the plasma membrane of specific cell types include muscular dystrophies (MDs), a group of genetic degenerative myopathies characterized by weakness and muscle atrophy without nervous system involvement. The three main types are pseudohypertrophic (Duchenne, Becker), limb-girdle, and facioscapulohumeral. For example, muscular dystrophies and muscular atrophies are characterized by a breakdown of the muscle cell membrane, i.e., they are characterized by leaky membranes, which are believed to result from a mutation in a component of the DAPC, i.e., dystrophin. Mutations in the sarcoglycans are also known to result in muscular dystrophies and leaky membranes. Accordingly, the invention provides for methods for treating or preventing diseases associated with mutations in dystrophin and/or in sarcoglycans or other component of DAPCs, in particular muscular dystrophies.

Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount.

The patient is mild to moderately weak. In DMD no protein is made and the patient is wheelchair-bound by age 13 and usually dies by age 20.

Another type of dystrophy that can be treated according to the methods of the invention includes congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features. Within the group of diseases classified as CMD, various forms have been individualized. The two more common forms are the occidental and the Japanese, the latter being associated with severe mental disturbances, and usually referred to as Fukuyama congenital muscular dystrophy (FCMD).

One form of congenital muscular dystrophy (CMD) has recently been characterized as being caused by mutations in the laminin alpha 2-chain gene. Laminin is a protein that associates with DAPCs. Thus, the invention also provides methods for treating diseases that are associated with abnormal molecules which normally associate with DAPCs.

Other muscular dystrophies within the scope of the invention include limb-girdle muscular dystrophy (LGMD), which represents a clinically and genetically heterogeneous class of disorders. These dystrophies are inherited as either autosomal dominant or recessive traits. An autosomal dominant form, LGMDIA, was mapped to 5q31-q33 (Speer, M. C. et al., Am. J. Hum. Genet. 50:1211, 1992; Yamaoka, L. Y. et al., Neuromusc. Disord. 4:471, 1994), while six genes involved in the autosomal recessive forms were mapped to 15q15.1 (LGMD2A) (Beckmann, J. S. et al., C. R. Acad. Sci. Paris 312:141, 1991), 2p16-p13 (LGMD2B) (Bashir, R. et al., Hum. Mol. Genet. 3:455, 1994), 13q12 (LGMD2C) (Ben Othmane, K. et al., Nature Genet. 2:315, 1992; Azibi, K. et al., Hum. Mol. Genet. 2:1423, 1993), 17q12-q21.33 (LGMD2D) (Roberds, S. L. et al., Cell 78:625, 1994; McNally, E. M., et. al., Proc. Nat. Acad. Sci. U.S.A. 91:9690, 1994), 4q12 (LG1MD2E) (Lim, L. E., et. al., Nat. Genet. 11:257, 1994; Bonnemann, C. G. et al. Nat. Genet. 11:266, 1995), and most recently to 5q33-q34 (LGMD2F) (Passos-Bueno, M. R., et. al., Hum. Mol. Genet. 5:815, 1996). Patients with LGMD2C, 2D and 2E have a deficiency of components of the sarcoglycan complex resulting from mutations in the genes encoding gamma-, alpha-, and beta-sarcoglycan, respectively. The gene responsible for LGMD2A has been identified as the muscle-specific calpain, whereas the genes responsible for LGMD1A, 2B and 2F are still unknown.

Yet other types of muscular dystrophies that can be treated according to the methods of the invention include Welander distal myopathy (WDM), which is an autosomal dominant myopathy with late-adult onset characterized by slow progression of distal muscle weakness. The disorder is considered a model disease for hereditary distal myopathies. The disease is linked to chromosome 2p13. Another muscular dystrophy is Miyoshi myopathya, which is a distal muscular dystrophy that is caused by mutations in the recently cloned gene dysferlin, gene symbol DYSF (Weiler et al. (1999) Hum Mol. Genet. 8: 871-7). Yet other dystrophies include Hereditary Distal Myopathy, Benign Congenital Hypotonia, Central Core disease, Nemaline Myopathy, and Myotubular (centronuclear) myopathy.

Other diseases that can be treated or prevented according to the methods of the invention include those characterized by tissue atrophy, e.g., muscle atrophy, other than muscle atrophy resulting from muscular dystrophies, provided that the atrophy is stopped or slowed down upon treatment with a therapeutic of the invention. Furthermore, the invention also provides methods for reversing tissue atrophies, e.g., muscle atrophies.

Muscle atrophies can result from denervation (loss of contact by the muscle with its nerve) due to nerve trauma; degenerative, metabolic or inflammatory neuropathy (e.g., GuillianBarre syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes.

Since muscle tissue atrophy and necrosis are often accompanied by fibrosis of the affected tissue, the reversal or the inhibition of atrophy or necrosis can also result in an inhibition or reversal of fibrosis.

In addition, the therapeutics of the invention may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexyline, and vincristine.

Neuromuscular dystrophies within the scope of the invention include myotonic dystrophy. Myotonic dystrophy (DM; or Steinert's disease) is an autosomal dominant neuromuscular disease which is the most common form of muscular dystrophy affecting adults. The clinical picture in DM is well established but exceptionally variable (Harper, P. S., Myotonic Dystrophy, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., Myotonic Dystrophy, 2nd ed., W. B. Saunders Co., London, 1989). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. This disease and the gene affected is further described in U.S. Pat. No. 5,955,265.

Another neuromuscular disease is spinal muscular atrophy ("SMA"), which is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy (see, e.g., U.S. Pat. No. 5,882,868).

The above-described muscular dystrophies and myopathies are skeletal muscle disorders. However, the invention also pertains to disorders of smooth muscles, e.g., cardiac myopathies, including hypertrophic cardiomyopathy, dilated cardiomyopathy and restrictive cardiomyopathy. At least certain smooth muscles, e.g., cardiac muscle, are rich in sarcoglycans. Mutations in sarcoglycans can result in sarcolemmal instability at the myocardial level (see, e.g., Melacini (1999) Muscle Nerve 22: 473). For example, animal models in which a sarcoglycan is mutated show cardiac creatine kinase elevation. In particular, it has been shown that delta-sarcoglycan (Sgcd) null mice develop cardiomyopathy with focal areas of necrosis as the histological hallmark in cardiac and skeletal muscle. The animals also showed an absence of the sarcoglycan-sarcospan (SG-SSPN) complex in skeletal and cardiac membranes. Loss of vascular smooth muscle SG-SSPN complex was associated with irregularities of the coronary vasculature. Thus, disruption of the SG-SSPN complex in vascular smooth muscle perturbs vascular function, which initiates cardiomyopathy and exacerbates muscular dystrophy (Coral-Vazquez et al. (1999) Cell 98: 465).

Similarly to delta-sarcoglycan negative mice, mice lacking .gamma.-sarcoglycan showed pronounced dystrophic muscle changes in early life (Hack et al. (1998) J Cell Biol 142: 1279). By 20 wk of age, these mice developed cardiomyopathy and died prematurely. Furthermore, apoptotic myonuclei were abundant in skeletal muscle lacking .gamma.-sarcoglycan, suggesting that programmed cell death contributes to myofiber degeneration. Vital staining with Evans blue dye revealed that muscle lacking .gamma.-sarcoglycan developed membrane disruptions like those seen in dystrophin-deficient muscle. It was also shown that the loss of gamma-sarcoglycan produced secondary reduction of beta- and delta-sarcoglycan with partial retention of .alpha.- and epsilon-sarcoglycan, indicating that beta-, .gamma.-, and delta-sarcoglycan function as a unit. Since the other components of the cytoplasmic membrane complex were functional, the complex could be stabilized by the presence of a therapeutic of the invention.

In addition to animal models, certain cardiomyopathies in humans have been linked to mutations in dystrophin, dystroglycans or sarcoglycans. For example, dystrophin has been identified as the gene responsible for X-linked dilated cardiomyopathy (Towbin J. A. (1998) Curr Opin Cell Biol 10: 131, and references therein). In this case, the dystrophin gene contained a 5'-mutation which results in cardiomyopathy without clinically-apparent skeletal myopathy (Bies et al. (1997) J Mol Cell Cardiol 29: 3175.

Furthermore, cardiomyopathy was also found in subjects having Duchenne's Muscular Dystrophy (associated with a mutated dystrophin), or other types of muscular dystrophies, such as Limb Girdle Muscular Dystrophy. For example, dilated cardiomyopathy was present in one autosomal dominant case and in three advanced autosomal recessive or sporadic patients, of whom two were found to have alpha sarcoglycan deficiency. Two of these three patients and three other cases showed ECG abnormalities known to be characteristic of the dystrophinopathies. A strong association between the absence of alpha sarcoglycan and the presence of dilated cardiomyopathy was found. In six autosomal dominant cases there were atrioventricular (AV) conduction disturbances, increasing in severity with age and in concomitant presence of muscle weakness. Pacemaker implantation was necessary in certain of these patients (see van der Kooi (1998) Heart 79: 73).

Therapeutics of the invention can also be used to treat or prevent cardiomyopathy, e.g., dilated cardiomyopathy, of viral origin, e.g., resulting from an enterovirus infection, e.g., a Coxsackievirus B3. It has been shown that purified Coxsackievirus protease 2A cleaves dystrophin in vitro and during Coxsackievirus infection of cultured myocytes and in infected mouse hearts, leading to impaired dystrophin function (Badorff et al. (1999) Nat Med 5: 320. Cleavage of dystrophin results in disruption of the dystrophin-associated glycoproteins .alpha.-sarcoglycan and beta-dystroglycan. Thus, cardiomyopathy could be prevented or reversed by administration of a therapeutic of the invention to a subject having been infected with a virus causing cardiomyopathy, e.g., by disruption of dystrophin or a protein associated therewith. Administration of the therapeutic could restabilize or reorganize the cytoplasmic membrane of affected cardiac cells.

Thus, the therapeutics of the invention can also be used to prevent or to treat smooth muscle disorders, such as cardiac myopathies, and to stop atrophy and/or necrosis of cardiac smooth muscle tissue. The treatment can also be used to promote survival of myocytes. The therapeutics of the invention can also be used to prevent or to treat heart failure, e.g., congestive heart failure. The DGC is known to be involved in heart failure. As such restoration of utrophin, nNOS and the sarcoglycans are expected to be beneficial in treatment of heart failure. Further, therapeutics of the invention are thought to help stabilize the DAPC in cardiac myocytes. Additionally, normalization of heart weight in mdx mice treated with biglycan has been observed.

Neurological disorders that can be treated according to the methods of the invention include polymyositis, and neurogenic disorders. Another neurological disease that can be treated is Alzheimers' disease. Another neurological disease that can be treated is Amyotrophic Lateral Sclerosis.

Other diseases that can be treated according to the methods of the invention include those in which the proteoglycan of the invention is present at abnormal levels, or has an abnormal activity, relative to that in normal subjects. For example, a disease or disorder could be caused by a lower level of biglycan, resulting in, e.g., unstable cytoplasmic membranes. Alternatively, a disease or disorder could result from an abnormally high level or activity of biglycan, resulting in, e.g., overstimulation of MuSK or over-aggregation of AChRs.

Yet other diseases or disorders that are within the scope of the invention include those that are associated with an abnormal interaction between a proteoglycan of the invention and another molecule (other than those of the DAPC or MuSK), e.g., a complement factor, such as C1q. For example, it has been shown that C1q interacts with biglycan (Hocking et al. (1996) J. Biol. Chem. 271: 19571). It is also known that binding of C1q to cell surfaces mediates a number of biological activities including enhancement of phagocytosis and stimulation of superoxide production. Thus, since biglycan binds to C1q, biglycan or another proteoglycan or core thereof, of the invention could be used to inhibit the binding of C1q to its receptor on cell surfaces to inhibit one or more of such biological activities. In addition, compounds of the invention which inhibit the interaction between C1q or other complement component and a cell surface can also be used to inhibit complement mediated necrosis of the cells and tissues containing such cells.

Also within the scope of the invention are methods for preventing or inhibiting infections of cells by microorganisms, e.g., viruses. For example, it has been shown that dystroglycan is a receptor via which certain microorganisms enter eukaryotic cells (Science (1998) 282: 2079). Thus, by administrating to a subject a therapeutic of the invention which occupies the site on dystroglycan molecules to which the microorganism binds, entering of the microorganism into the cell can be inhibited. This method can be used, e.g., to prevent or inhibit Lassa Fever virus and lymphocytic choriomeningitis virus (LCMV) infection, as well as infection by other arenaviruses, including Oliveros, and Mobala. Soluble alpha-dystroglycan was shown to block both LCMV and LFV infection (Science (1998) 282: 2079).

In addition to cell cultures, e.g., established from patients having, e.g., a muscular dystrophy, various animal models can be used to select the most appropriate therapeutic for treating a disease. In particular, to identify a therapeutic for use in preventing or treating a muscular dystrophy or cardiomyophaty associated with a mutated or absent DAPC component or, mice having mutated versions of these proteins, or having null mutations in the genes encoding these proteins, can be used. For example, mice having a disrupted sarcoglycan, such as delta-sarcoglycan, can be used. Such mice are described, e.g., Coral-Vazquez et al. (1999) Cell 98: 465. Alternatively, mice deficient in dystrophin (mdx mice), or in .alpha.- or .gamma.-sarcoglycans can be used. Such mice have been described herein and in the literature. Additional mice can be made according to known methods in the art. In an illustrative embodiment to identify therapeutics, different therapeutics are administered to delta-sarcoglycan null mice, and the effect of the therapeutics are evaluated by studying cardiac function. Another animal model that can be used for this purpose is the cardiomyopathic hamster that does not express delta-sarcoglycan due to a genomic deletion. This rat is an animal model for autosomal recessive cardiomyopathy, and is further described in Sakamoto et al. FEBS Lett 1999 (1999) 44: 124.

Effective Dose and Administration of Therapeutic Compositions

The above-described diseases or disorders can be treated or ameliorated in a subject by administering to the subject a pharmaceutically efficient amount of a bigylcan therapeutic of the invention. Depending on whether the disease is caused by higher levels or activity or by lower levels or activity of biglycan, an agonist or an antagonist biglycan therapeutic is administered to a subject having the disease. Although a person of skill in the art will be able to predict which therapeutic to administer for treating any of the diseases of the invention, tests can be performed to determine the appropriate therapeutic to administer. Such tests can use, e.g., animal models of the disease. Alternatively, in cases where diseases are due to a mutation in, e.g., biglycan, in vitro tests can be undertaken to determine the effect of the mutation. This will allow the determination of what type of therapeutic should be administered to a subject having this type of mutation.

Another manner of administering a therapeutic of the invention to a subject is by preparing cells expressing and secreting the proteoglycan of interest, inserting the cells into a matrix and administering this matrix to the subject at the desired location. Thus, cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J. Biomed. Mater. Res. 27(10):1213-24 (HepG2 cells/hydroxyethyl methacrylate-methyl methacrylate membranes); Chang et al, 1993, Hum Gene Ther 4(4):433-40 (mouse Ltk-cells expressing hGH/immunoprotective perm-selective alginate microcapsules; Reddy et al, 1993, J Infect Dis 168(4):1082-3 (alginate); Tai and Sun, 1993, FASEB J 7(11):1061-9 (mouse fibroblasts expressing hGH/alginate-poly-L-lysine-alginate membrane); Ao et al, 1995, Transplanataion Proc. 27(6): 3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37-47 (polymer-encapsulated PC12 cells); Sagen et al, 1993, J Neurosci 13(6):2415-23 (bovine chromaffin cells encapsulated in semipermeable polymer membrane and implanted into rat spinal subarachnoid space); Aebischer et al, 1994, Exp Neurol 126(2):151-8 (polymer-encapsulated rat PC12 cells implanted into monkeys; see also Aebischer, WO 92/19595); Savelkoul et al, 1994, J Immunol Methods 170(2):185-96 (encapsulated hybridomas producing antibodies; encapsulated transfected cell lines expressing various cytokines); Winn et al, 1994, PNAS USA 91(6):2324-8 (engineered BHK cells expressing human nerve growth factor encapsulated in an immunoisolation polymeric device and transplanted into rats); Emerich et al, 1994, Prog Neuropsychopharmacol Biol Psychiatry 18(5): 935-46 (polymer-encapsulated PC12 cells implanted into rats); Kordower et al, 1994, PNAS USA 91(23):10898-902 (polymer-encapsulated engineered BEM cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more proteoglycans of the host species and/or from viral proteins or proteins from species other than the host species.

Alternatively, the therapeutic is a nucleic acid encoding the core of a proteoglycan of the invention. Thus, a subject in need thereof, may receive a dose of viral vector encoding the protein of interest, which may be specifically targeted to a specific tissue, e.g., a dystrophic tissue. The vector can be administered in naked form, or it can be administered as a viral particle (further described herein). For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In yet another embodiment, cells are obtained from a subject, modified ex vivo, and introduced into the same or a different subject. Additional methods of administration of the therapeutic compounds are set forth below.

Toxicity: Toxicity and therapeutic efficacy of compounds of the invention can be determined by standard pharmaceutical procedures in cell cultures or experimental animals, e.g., for determining The Ld50 (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular, where the therapeutic is administered for potentiating AChR aggregation, it is desirable to establish the dose that will result in stimulation, if desired, or inhibition, if desired. Tests can then be continued in medical tests. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions: Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic gene encoding a proteoglycan of the invention can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054-3057). A gene encoding a proteoglycan of the invention can be delivered in a gene therapy construct by electroporation using techniques described, for example, by Dev et al. ((1994) Cancer Treat Rev 20:105-115).

A preferred mode of delivering DNA to muscle cells include using recombinant adeno-associated virus vectors, such as those described in U.S. Pat. No. 5,858,351. Alternatively, genes have been delivered to muscle by direct injection of plasmid DNA, such as described by Wolff et al. (1990) Science 247:1465-1468; Acsadi et al. (1991) Nature 352:815-818; Barr and Leiden (1991) Science 254:1507-1509. However, this mode of administration generally results in sustained but generally low levels of expression. Low but sustained expression levels are expected to be effective for practicing the methods of the invention.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic Methods

Based at least on the observation that biglycan binds to at least one component of DAPCs, protein complexes which are critical for maintaining the integrity of plasma membranes, the invention provides diagnostic methods for determining whether a subject has or is likely to develop a disease or condition which is characterized by, or associated with, plasma membrane instability, in particular, abnormal or unstable DAPCs, such as muscular dystrophies. Furthermore, it has been observed in an animal model for muscular dystrophy, which lacks dystrophin, that the amount of the proteoglycan biglycan is elevated, and thereby believed to be a compensatory mechanism.

Furthermore, based at least on the observation that biglycan binds to, and phosphorylates MuSK and potentiates agrin-induced MuSK phosphorylation, and that biglycan stimulates agrin-mediated AChR aggregation, the invention also provides diagnostic methods for determining whether a subject has or is likely to develop a disease or condition which is characterized by abnormal synapses or neuromuscular junctions, e.g., neurological or neuromuscular diseases.

Accordingly, the identification of abnormal levels or activity of the proteoglycan of the invention in a subject would indicate that the subject has, or is likely to develop a disease or condition relating to abnormal or unstable DAPCs. Diseases can be characterized by a high levels of proteoglycan of the invention, e.g., if the cell compensates for the lack of another DAPC component or molecule associating therewith, e.g., as seen in dystrophin negative mice. Alternatively, a high level or activity of proteoglycan of the invention can at least be part of the cause of the disease.

In addition, an elevated level or activity of a proteoglycan of the invention could be associated with, or be at least in part, the cause of neurological or neuromuscular diseases, e.g., by overstimulating AChR aggregation and/or activating MuSK.

Diseases are also likely to be caused or associated with a lower level or activity of proteoglycan of the invention, which may, e.g., cause DAPCs to be more unstable than those on cells of subjects having a normal amount or activity of the proteoglycan of the invention. Accordingly, a lower level or activity of the proteoglycan of the invention in cells of a subject would result in leaky membranes.

A lower level or activity of the proteoglycan of the invention could also result in insufficient AChR aggregation and/or insufficient MuSK activation, thereby resulting in abnormal synapses or neuromuscular junctions. Such situations can thus result in neurological or neuromuscular diseases, and result, e.g., in atrophy of tissues.

As used herein, the term "diagnostic assay" refers to the specific use of the methods described herein to identify an individual predisposed to a disease, such as a muscular disorder, a neuromuscular disorder or a neurological disorder. Such diagnostic assays are particularly useful as prenatal diagnostic assays, which can be used to determine whether a fetus is predisposed to one or more of these disorders. For prenatal diagnosis, for example, a sample can be obtained by biopsy of muscle tissue from the fetus or by biopsy of placenta from the pregnant mother.

In one embodiment, the method comprises determining the level of, or the biological activity of a proteoglycan of the invention relative to that in non-affected subjects, or determining whether the proteoglycan or gene encoding it contains a mutation, or abnormal glycan side chains.

A patient sample may be any cell, tissue, or body fluid but is preferably muscle tissue, cerebrospinal fluid, blood, or a blood fraction such as serum or plasma. As used herein, the term "sample" refers to a specimen obtained from a subject, which can be a human subject. In general, a tissue sample, which can be obtained, for example, by biopsy of muscle or placenta of an individual suspected of being predisposed to a disorder, is a suitable sample. In many cases, it is useful to prepare the sample as a tissue section, which can be examined by histologic analysis. Alternatively, proteins or nucleic acids can be extracted from a sample and can be examined using methods such as gel electrophoresis and appropriate "blotting" methods, which are well known in the art and described in detail below.

A sample can be obtained from a normal subject or from a test subject, who is suspected of being predisposed to a disorder, such as a muscular, neuromuscular or neurological disorder, and is being examined for altered expression or localization of the proteoglycan of the invention or altered expression of the mRNA encoding the proteoglycan of the invention.

A sample obtained from a normal subject can be used as a "control" sample, which is useful for comparison with a sample obtained from a test subject. A control sample can be, for example, a muscle sample or a placenta sample, which is obtained from an age- and sex-matched individual who does not exhibit and is not predisposed to a disorder, such as a muscular, neuromuscular, or neurological disorder. A control sample exhibits a level of expression and a pattern of expression of the proteoglycan of the invention and a level of expression of the proteoglycan mRNA that is characteristic of the human population in general and does not significantly deviate from the normal levels of expression or pattern of localization expected for a person in the population. It is expected that, after a statistically significant number of control samples have been examined, an amount of expression of the proteoglycan of the invention per unit of a sample will be determined to be normal for a control sample. As used herein, a "normal" amount of proteoglycan of the invention in a control sample means an amount that is within an expected range for a person that is not predisposed to a disorder, e.g., a muscular, neuromuscular, or neurological disorder.

Altered expression of the proteoglycan of the invention in a sample obtained from a test subject can be identified qualitatively by visually comparing, for example, photomicrographs of an immunohistochemically stained control sample with the sample obtained from the test subject. Alternatively, altered expression of proteoglycan of the invention can be measured quantitatively using, for example, densitometric analysis. Altered expression of proteoglycan of the invention protein also can be determined using methods of gel electrophoresis and, if desired, immunoblot analysis. Such methods are well known in the art.

Methods for the determination of levels of dystrophin and dystrophin-associated proteins are carried out by conventional techniques. Such techniques are disclosed, for example, in U.S. Pat. Nos. 5,187,063; 5,260,209; and 5,308,752, the disclosures of which are incorporated herein by reference. International Publication Number WO 89/06286 also discloses such conventional techniques, as well as the nucleic sequence encoding dystrophin.

Altered localization of the proteoglycan of the invention in a sample also can be determined. As used herein, the term "localization" refers to the pattern of deposition of the proteoglycan of the invention in a sample. The localization of the proteoglycan of the invention also can be determined qualitatively or quantitatively. "Altered" localization refers to a pattern of deposition of the proteoglycan of the invention in a sample that is different from the pattern of localization observed in a control sample.

The level of expression mRNA encoding the proteoglycan of the invention can be determined and can be used to identify an individual that is predisposed to a disorder, such as muscular, neuromuscular, or neurological disorder. Methods for determining the level of expression of proteoglycan mRNA in a sample are well known in the art and include, for example, northern blot analysis, which can be used to determine whether proteoglycan mRNA is expressed at a normal level in a test sample. Northern blot analysis also can be used to determine whether the proteoglycan mRNA that is expressed in a cell is a full length transcript. For example, an RNA sample obtained from a tissue sample can be contacted with a nucleic acid probe that hybridizes to the mRNA encoding the proteoglycan of the invention. One skilled in the art would know that the probe can be a DNA or RNA probe and can be prepared from a cDNA encoding the proteoglycan or can be synthesized as an oligonucleotide. In addition, the skilled artisan would recognize that such hybridization should be performed under stringent conditions, which can be determined empirically (see, for example, Sambrook et al., Molecular Cloning: A laboratory manual (Cold Spring Harbor Laboratory Press 1989), which is incorporated herein by reference). Methods for isolating intact total RNA and poly A+ mRNA and for performing Northern blot analysis are well known in the art (Sambrook et al., 1989).

A sensitive method of determining the level of expression of mRNA encoding the proteoglycan of the invention in a sample is the reverse transcriptase-polymerase chain reaction (RT-PCR), which is well known in the art (see, for example, H. A. Erlich, PCR Technology: Principles and applications for DNA amplification (Stockton Press, 1989), which is incorporated herein by reference; see chap. 8). The RT-PCR method is particularly useful for examining a sample that fails to give a detectable signal by northern blot analysis. Due to the amplification steps involved in PCR analysis, a rare proteoglycan mRNA can be identified in a sample.

Methods for determining levels of proteoglycan of the invention can use, e.g., antibodies binding to the proteoglycan of the invention. An antibody can be used in connection with a conventional assay for the determination of levels of antigen in a tissue of interest, e.g., muscle tissue. Any method which enables the determination of protein levels present in muscle tissue based on antibody binding is useful in connection with the present invention. Preferred methods include Western blotting, immunocytochemical analysis and enzyme-linked immunoadsorbent assay (ELISA).

For assays which require solubilized extracellular matrix (e.g., ELISA and Western blotting), the amount of muscle obtained by biopsy should be sufficient to enable the extraction of the proteoglycan of the invention in a quantity sufficient for analysis. In an illustrative embodiment, the muscle tissue is homogenized by mechanical disruption using an apparatus such as a hand operated or motor driven glass homogenizer, a Waring blade blender homogenizer, or an ultrasonic probe. Homogenization can be carried out, for example, in a buffer having a pH of about 11 or 12, as further described in the Examples. The buffer can further comprise protease inhibitors, e.g., 1 mM PMSF, 0.75 mM benzamidine, 1 mu g/ml aprotinin, 1 mu g/ml of leupeptin, 1 mu g/ml of pepstatin A. The incubation is then carried out, e.g., on ice for 2 hr. Following centrifugation, extracellular matrix solubilized in this manner can then be processed by conventional methods for use, for example, in Western blotting or ELISA analytical formats.

The solubilized extracellular matrix components, prepared as described above can be analyzed by Western blotting by first separating the components on a 3-12% SDS polyacrylamide gel (Laemmli (1970) Nature 227, 680) followed by transfer to a solid support, such as a nitrocellulose membrane, forming an exact replica of the original protein separation but leaving the transferred proteins accessible for further study. This solid support bearing the transferred protein components is referred to as an immunoblot. The detection of transferred proteins can be accomplished by the use of general protein dyes such as Amido black or Coomassie brilliant blue. Antibodies which are specific for the proteoglycan of the invention can be labeled with a detectable reporter group and used to stain the protein transferred to the solid support. Alternatively, unlabeled antibodies specific for the proteoglycan of the invention are incubated with an immunoblot under conditions appropriate for binding. The specific binding of these antibodies to the muscle tissue sample can be detected through the use of labeled secondary antibodies by conventional techniques.

The methods of the present invention can also be practiced in an enzyme-linked immunoadsorbent assay (ELISA) format. In this format, antibodies against the proteoglycan of the invention are adsorbed to a solid support, in most cases a polystyrene microtiter plate. After coating the support with antibody and washing, a solubilized sample is added. Proteoglycan of the invention, if present, will bind to the adsorbed antibodies. Next, a conjugate that will also bind to the proteoglycan of interest is added. A conjugates can be an antibody molecule which binds to the proteoglycan of the invention, and to which an enzyme is covalently bound. After addition of a chromogenic substrate for the enzyme, the intensity of the colored reaction products generated will be proportional to the amount of conjugated enzyme and thus indirectly to the amount of bound proteoglycan of the invention. Since the intensity of the developed color is proportional to the amount of proteoglycan of the invention present, determination of the intensity of the color produced by a standard series of concentrations of proteoglycan of the invention will allow the calculation of the amount of proteoglycan of the invention in an unknown sample. Many variations of this assay exist as described in Voller, A., Bidwell, D. E. and Bartlett, A., The Enzyme Linked Immunoadsorbent Assay (ELISA): A guide with abstracts of microplate applications, Dynatech Laboratories, Alexandria, Va. (1979).

Alternatively, tissue specimens (e.g., human biopsy samples) can be tested for the presence of the components of the DAPC complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air-dried and then incubated with an antibody preparation against the proteoglycan (primary antibody) of the invention in a humidified chamber at room temperature. The slides are layered with a preparation of fluorescently labeled antibody directed against the primary antibody. Labeled secondary antibodies are also useful for detection. The staining pattern and intensities within the sample can be determined by fluorescent light microscopy.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in genes, e.g., a gene encoding a proteoglycan of the invention, can be identified, by determining the nucleotide sequence of genes in populations of individuals. If a polymorphic region, e.g., SNP, is identified, then the link with a specific disease can be determined by studying specific populations of individuals, e.g., individuals which developed a specific disease, such a muscular, neuromuscular, or neurological disease. A polymorphic region can be located in any region of a gene, e.g., exons, in coding or non coding regions of exons, introns, and promoter region.

It is likely that genes encoding proteoglycans of the invention comprise polymorphic regions, specific alleles of which may be associated with specific diseases or conditions or with an increased likelihood of developing such diseases or conditions. Thus, the invention provides methods for determining the identity of the allele or allelic variant of a polymorphic region of a gene encoding a proteoglycan of the invention in a subject, to thereby determine whether the subject has or is at risk of developing a disease or disorder associated with a specific allelic variant of a polymorphic region.

In an exemplary embodiment, there is provided a nucleic acid composition comprising a nucleic acid probe including a region of nucleotide sequence which is capable of hybridizing to a sense or antisense sequence of a gene encoding a proteoglycan of the invention or naturally occurring mutants thereof, or 5' or 3' flanking sequences or intronic sequences naturally associated with the subject proteoglycan genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect alterations or allelic variants at either the genomic or mRNA level, including deletions, substitutions, etc., as well as to determine mRNA transcript levels.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Production of T2-rhBGN

Stable CHO clones expressing T2-rhBGN produce a mixture of two forms herein referred to as M and D or M-rhBGN and D-rhBGN.

Figure 1:
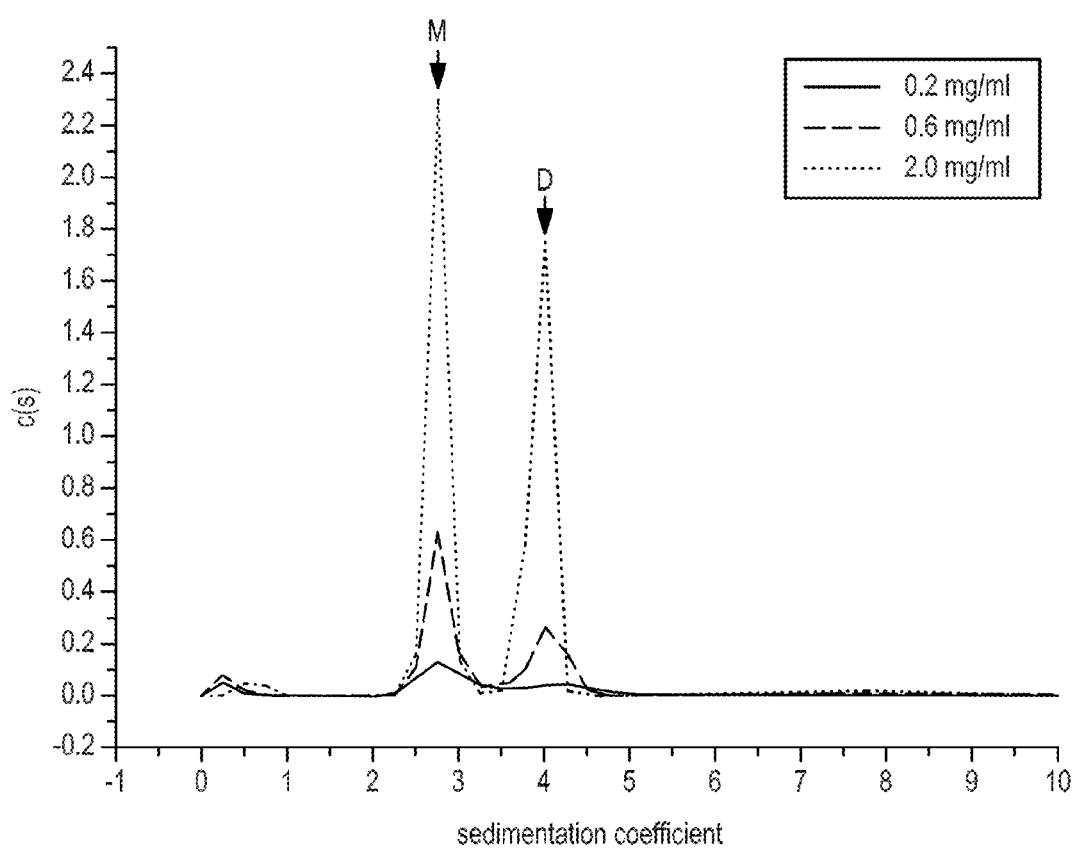
FIG. 1. Analytical ultracentrifugation of HIC pool purified from CHO clone 57. HIC pool in 20 mM Tris, pH 8.0, 0.5M NaCl was analyzed by AUC at 0.2, 0.6 and 2 mg/ml. The HIC pool resolved into 2 sedimentation peaks: M and D. Analysis of the sedimentation at three concentrations showed that the dissociation constant for M-D exchange in the HIC pool was ~50 µM.

T2-rhBGN was purified from conditioned media of CHO clone 57 and 171 and HEK 293 clone 2 by a combination of anion exchange and hydrophobic interaction (HIC). Analytical ultracentrifugation (AUC) of HIC pool purified from CHO Clone 57 resolved into two sedimentation peaks: M with a sedimentation coefficient: $s_{20,w} \approx 2.88$ and D with coefficient $s_{20,w} \approx 4.28$ (FIG. 1). Analysis of the sedimentation at three concentrations (0.2, 0.2, and 2 mg/ml) showed that the dissociation constant for M-D exchange in the HIC pool was ~50 µM. Experiments were performed at 20° C., in a Beckman Optima XL-I analytical ultracentrifuge. Spin Analytical charcoal upon 12 mm double-sector centerpieces were used in an eight-hole AN 50 Ti rotor at 45,000 rpm. Radial absorption scans were measured at λ=280 nm. Sedfit 12.44 was used for data analysis, with a 68% confidence limit (analyticalultracentrifugation.com). Sedimentation coefficients were corrected to standard $s_{20,w}$ conditions using the experimental buffer density and buffer viscosity as calculated with SEDNTERP (sednterp.unh.edu). Buffer: 20 mM Tris, pH 8, 0.5M NaCl; viscosity=0.01002 Poise; density=1.004989 g/mL. Partial specific volume, v-bar=0.74413 mL/g calculated from amino acid composition with Sednterp.

Figure 2A:
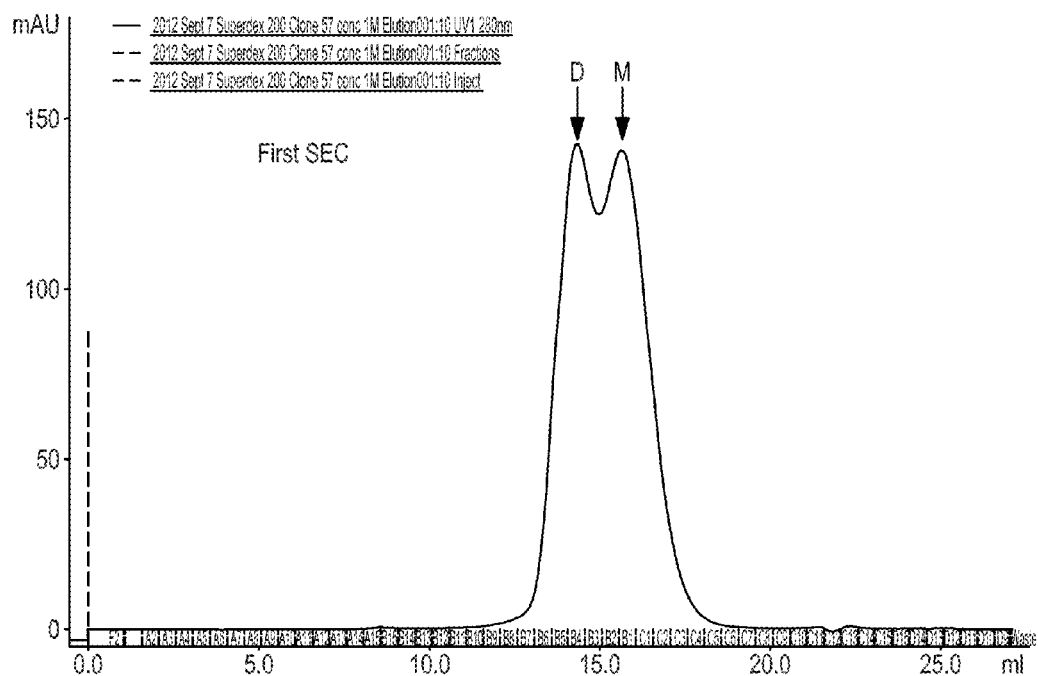
FIG. 2a-b. Purification of M- and D-rhBGN by size exclusion chromatography. CHO clone 57 HIC pool in 20 mM Tris, pH 8.0, 0.5M NaCl was applied to a Superdex™
Figure 2B:
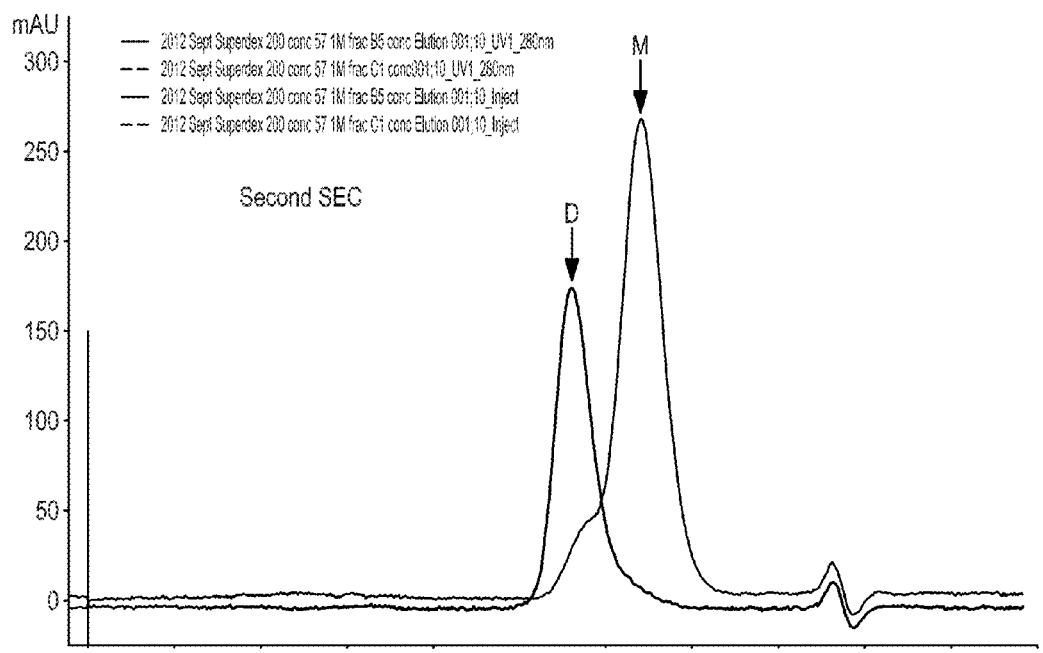

Further analysis of the HIC pool by size exclusion chromatography (SEC) showed that the HIC pool resolved into two distinguishable peaks that corresponded to M and D (FIG. 2). Clone 57 HIC pool in 20 mM Tris, pH 8.0, 0.5M NaCl was applied to a Superdex 200 10/300 GL (GE Healthcare) equilibrated with 20 mM Tris, pH 8.0, 1M NaCl. In the first SEC analysis (FIG. 1a), T2-rhBGN resolved into two discrete, partially overlapping peaks that eluted at ~18.7 (D) and 20.4 ml (M). The fractions corresponding to these two peaks were each re-run on the SEC column. Highly discrete peaks were observed with the same elution profiles (FIG. 1b). These analyses indicate that M and D can be enriched by SEC and there is little exchange between the two forms.

EXAMPLE 2

M- and D-rhBGN Are Chemically Distinct

The M and D forms purified from CHO clone 57 HIC pool over two size exclusion columns were further analyzed by Capillary Electrophoresis (FIG. 3) was conducted using an Agilent Bioanalyzer 2100 and Agilent Protein 80 assay kit under non-reducing conditions according to manufacturer's protocols. The apparent molecular weight and mobility of D-rhBGN (65.5 kd, 31.00, respectively) was greater than that of M-rhBGN (60 kd, 30.44, respectively), indicating differential posttranslational modification of the two forms.

The M and D forms were characterized by N-linked oligosaccharide profiling analysis (FIG. 4). Approximately 250 µg of M- and D-rhBGN were digested into glycopeptides with trypsin at 37° C. overnight. The glycopeptides were purified with a C18 cartridge, eluted in sequential elutions of 20%, 40%, and 100% isopropanol, combined, and dried. N-glycans were released by enzymatic cleavage with PNGase F, and then purified of contaminants with a C18 sep-pak cartridge. The carbohydrate fraction was eluted with 5% acetic acid and dried by lyophilization. Released N-linked oligosaccharides were permethylated based on a previously described method (Anumula and Taylor, 1992). The glycans were dried with nitrogen gas and profiled by MALDI-TOF analysis. MALDI/TOF-MS was performed in the reflector positive ion mode using α-dihyroxybenzoic acid (DHBA, 20 mg/mL solution in 50% methanol:water) as a matrix. All spectra were obtained by using a ABISciex 5800 MALDI/TOF-TOF. The percentages of each glycan were calculated for each sample. M and D showed varying amounts of complex-type glycans, branching and sialic acid.

EXAMPLE 3

M-rhBGN is Highly Active in Bioassays

M-rhBGN purified from CHO clone 171 by two rounds of SEC was analyzed (FIG. 5) by an in-vitro bioassay for biglycan activity where the ability of biglycan to potentiate agrin-induced AChR clustering in cultured H2K myotubes is measured based on the method described in (Amenta et al., J. Neuroscience, 2012). M-rhBGN showed a robust and broad dose-response. Activity was observed in a 30-fold range of ≥50% of maximal activity between 0.016-0.512 µg/ml. (FIG. 5.)

EXAMPLE 4

D-rhBGN Shows Low Bioactivity

The SEC fractions containing D-rhBGN were analyzed by the bioassay describe above. As shown in FIG. 5, there was only low activity (≤25% of maximal) across the entire concentration range tested (0.004-0.512 µg/ml).

EXAMPLE 5

Evaluation of In-Vivo Efficacy of the M-rhBGN

In vivo efficacy of M-rhBGN purified from HEK-293 Clone 2 by size exclusion chromatography was evaluated in an in-vivo efficacy model in mdx mice (FIG. 6). P18 male mdx mice were IP injected at P18 and P25 with the indicated doses of M-rhBGN or vehicle only. Diaphragms were harvested at P32 and flash frozen in liquid nitrogen cooled isopentane. Frozen sections were prepared as previously described (Mercado et. al., 2006) and H&E stained. Sections were observed using a Nikon Eclipse E800 microscope and montages of sections were acquired with NIS Elements. The percentage of myofibers with centrally located nuclei were scored by workers blind to experimental conditions. All of the myofibers in a section from the mid-belly of the muscle were counted. M-rhBGN reduced the percentage of myofibers with central nuclei (*$p<0.05$, 1-way ANOVA analysis with post-hoc Dunnett's Multiple Comparison, n=7-10 animals/group). There was a statistically significant response across a 20-fold range (0.5-10 mg/kg).

EXAMPLE 6

Evaluation of Structure of M- and D-rhBGN

The structure M- and D-rhBGN purified from CHO Clone 57 by size exclusion chromatography was evaluated using circular dichroism (CD) (FIG. 7). The 2 samples were analyzed by near and far UV CD. CD measurements were carried out at room temperature using 2 cm cell for near UV CD and 0.02 cm cell for far UV CD. After subtracting solvent spectrum (20 mM Tris, 0.5 M NaCl, pH 8.0), the sample spectrum was converted to the mean residue ellipticity (CD intensity per amino acid) using the protein concentration, the path-length of the cell and the mean residue weight (112.2): note that this calculation normalizes for the different protein concentrations. The near and far UV CD spectra differ for M- and D-rhBGN indicating they have different structures.

Although the invention has been described with reference to the above example, it will be understood that modifications and variations are encompassed within the spirit and scope of the invention. Accordingly, the invention is limited only by the following claims.

What is claimed is:

1. A composition comprising a biglycan variant polypeptide lacking glycosaminoglycan side chains, wherein the biglycan variant polypeptide consists essentially of a monomeric form of a biglycan variant polypeptide that has an amino acid sequence as set forth in amino acid residues 38-368 of SEQ ID NO: 4 and a molecular weight of approximately 40-44 kDa and potentiates at least 50% of maximal agrin-induced acetylcholine receptor (AChR) clustering at a concentration of biglycan variant polypeptide from about 0.016 to 0.512 µg/ml.

2. The composition of claim 1, wherein the monomeric form of the biglycan variant polypeptide potentiates at least 50% of maximal agrin-induced AChR clustering at a concentration of from about 0.016 to 0.128 µg/ml.

3. The composition of claim 1, wherein the monomeric form of the biglycan variant polypeptide potentiates at least 50% of maximal agrin-induced AChR clustering at a concentration of from about 0.016 to 0.064 µg/ml.

4. A pharmaceutical composition comprising
a) the composition of claim 1; and
b) a pharmaceutically acceptable carrier.

* * * * *